US007674626B2

(12) United States Patent
Papkovsky et al.

(10) Patent No.: US 7,674,626 B2
(45) Date of Patent: Mar. 9, 2010

(54) OXYGEN SENSITIVE PROBE

(75) Inventors: Dmitri Boris Papkovsky, Blarney (IE);
Richard Fernandes, Newbridge (IE)

(73) Assignee: Luxcel Biosciences Limited,
Newbridge, County Kildare (IE)

( * ) Notice: Subject to any disclaimer, the term of this patent is extended or adjusted under 35 U.S.C. 154(b) by 837 days.

(21) Appl. No.: 11/218,585

(22) Filed: Sep. 6, 2005

(65) Prior Publication Data

US 2006/0002822 A1 Jan. 5, 2006

Related U.S. Application Data

(63) Continuation of application No. PCT/IE2004/000031, filed on Mar. 5, 2004.

(30) Foreign Application Priority Data

Mar. 7, 2003 (IE) .................................. 2003/0166

(51) Int. Cl.
*G01N 21/64* (2006.01)
*G01N 31/22* (2006.01)

(52) U.S. Cl. .................... 436/68; 436/905; 436/127; 422/82.08; 422/82.05; 422/68.1; 422/50

(58) Field of Classification Search ................ 436/68, 436/905, 127; 435/40.5; 424/178.1; 422/82.08, 422/82.05, 68.1, 50
See application file for complete search history.

(56) References Cited

U.S. PATENT DOCUMENTS

| | | | |
|---|---|---|---|
| 4,003,707 A | 1/1977 | Lübbers et al. | |
| 4,587,101 A | 5/1986 | Marsoner et al. | ............... 422/56 |
| 4,810,655 A | 3/1989 | Khalil et al. | |
| 4,947,850 A | 8/1990 | Vanderkooi et al. | |
| 5,030,420 A | 7/1991 | Bacon et al. | |
| 5,210,015 A | 5/1993 | Gelfand et al. | |
| 5,232,839 A | 8/1993 | Eden et al. | |
| 5,371,016 A | 12/1994 | Berndt | |
| 5,538,848 A | 7/1996 | Livak et al. | |
| 5,718,842 A | 2/1998 | Papkovsky et al. | |
| 5,837,865 A | 11/1998 | Vinogradov et al. | |
| 5,882,922 A | 3/1999 | Tyndorf et al. | |
| 5,925,517 A | 7/1999 | Tyagi et al. | |
| 6,080,574 A | 6/2000 | Berndt | |
| 6,150,097 A | 11/2000 | Tyagi et al. | |
| 6,165,741 A | 12/2000 | Wilson et al. | |
| 6,362,175 B1 | 3/2002 | Vinogradov et al. | |
| 6,395,555 B1 | 5/2002 | Wilson et al. | |
| 6,582,930 B1* | 6/2003 | Ponomarev et al. | ........ 435/40.5 |
| 2004/0043030 A1* | 3/2004 | Griffiths et al. | .......... 424/178.1 |
| 2005/0064582 A1 | 3/2005 | Wittwer et al. | |

FOREIGN PATENT DOCUMENTS

| | | |
|---|---|---|
| EP | 0 070 685 | 10/1985 |
| EP | 0344313 A1 | 12/1989 |
| EP | 0 232 967 | 4/1993 |
| EP | 0 745 690 | 12/1996 |
| EP | 1 295 941 | 3/2003 |
| WO | 97/45539 | 12/1997 |
| WO | WO98/15645 | 4/1998 |
| WO | 98/26708 | 6/1998 |
| WO | 03/019138 | 3/2003 |
| WO | 03/043402 | 5/2003 |
| WO | 03/059518 | 7/2003 |
| WO | 2004/079349 | 9/2004 |

OTHER PUBLICATIONS

Hynes et al., Fluorescence-Based Cell Viability Screening Assays Using Water-Soluble Oxygen Probes, Journal of Biomolecular Screening, 2003, 8(3), p. 264-272.*
O'Donovan et al., Phosphorescent oxygen-sensitive material for biological applications, May 9, 2005, 15, 2946-2951.*
Vanderkooi, et al., An Optical Method for Measurement of Dioxygen Concentration Based Upon Quenching of Phosphorescence, The Journal of Biological Chemistry, vol. 252, No. 12, p. 5476-5492.*
Papkovsky, D. et al., Emerging Applications of Phosphorescent Metalloporphyrins, Journal of Fluorescence, Jul. 2005, vol. 15, No. 4, 569-584.*
Hynes J. et al., Fluorescence-Based Cell Viability Screening Assays Using Water-Souble Oxygen Probes, The Society for Biomolecular Screening, 2003, 8(3), 264-272.*
Vanderkooi et al, Jour of Biol Chem, vol. 262, No. 12, 1987, pp. 5476-5492, An Optical Method for Measurement of Dioxygen . . . .
Dunphy et al, Analytical Biochemistry 310, 2002, pp. 191-198, Oxyphor R2 and G2: phosphors for measuring oxygen by . . . .
Rietveld et al, Tetrahedron 59, 2003, pp. 3821-3831, Dendrimers with tetrabenzoporphyrin cores: near infrared phosphors for . . . .
Vinogradov et al, Biophysical Jour, vol. 70, Apr. 1996, pp. 1609-1617, Noninvasive Imagining of the Distribution in Oxygen in . . . .
Burke, M. et al, Analytical Biochemistry 320, 2003, pp. 273-280 Evaluation of the phosphorescent palladium (II) . . . .
Cao, Y. et al, The Analyst 129, 2004, pp. 745-750, Poly(decylmethacrylate)—based fluorescent Pebble swarm nanocensors . . . .
Hogan, Michael C., J. Appl. Physiol 86, 1999, pp. 720-724, Phosphorescence quenching method for measurement of . . . .
Hurley, D. J. & Yitzhak T., J. Am. Chem. Soc. 124, 2002, pp. 13231-13241, Donor/Acceptor Interactions in Systematically . . . .
Hynes, J. et al., J. of Biomol. Screen. 8(3), 2003, pp. 264-272, Fluorescence-Based Cell Viability Screening Assays Using Water . . . .
Hynes, J. et al., Toxicological Sci. 92(1), 2006, pp. 186-200 Investigation of Drug-Induced Mitochondrial Toxicity-Using . . . .

(Continued)

*Primary Examiner*—Walter D Griffin
*Assistant Examiner*—Christine T Mui
(74) *Attorney, Agent, or Firm*—Jacobson Holman PLLC (57) ABSTRACT

An oxygen sensitive probe comprises a monofunctional derivative of an oxygen-sensitive photoluminescent dye covalently attached to a water soluble and/or hydrophilic macromolecular carrier. The probe may be a chemical conjugate of a monofunctional phosphorescent porphyrin dye and a poly(ethyleneglycol), polypeptide or polysaccharide.

63 Claims, 6 Drawing Sheets

OTHER PUBLICATIONS

Hynes, J. et al., Toxicol. In Vitro 20, 2006, pp. 785-792, The use of fluorescence-based oxygen uptake assay in the . . . .

Ji, J. et al., Anal. Chem. 73, 2001, pp. 3521-3527, Molecular Oxygen-Sensitive Fluorescent Lipobeads for Intracellular . . . .

Johannes, T. et al., J. Appl. Physiol. 100, 2006, pp. 1301-1310 Dual-wavelength phosphorimetry for determination of cortical . . . .

John, G. et al., Biotechnology and Bioeng. 81(7), 2003, pp. 829-836, Integrated Optical Sensing of Dissolved Oxygen in . . . .

Koo, Y. et al., Anal. Chem. 76, 2004, pp. 2498-2505, Real-Time Measurements of Dissolved Oxygen Inside Live Cells by . . . .

Lee, W. et al., J. Mater. Chem. 3(10), 1993, pp. 1031-1035, Halogenated Platinum Porphyrins as Sensing Materials for . . . .

Martsev, S. et al., J. of Immun. Methods 186, 1995, pp. 293-304, Modification of monoclonal and polyclonal IgG with palladium . . . .

Nurmi, J. et al., Nucleic Acids Research 28(8), 2000, pp. i-vi, A new label technology for the detection of specific . . . .

Nurmi, J. et al., Anal. Chem. 74, 2002, pp. 3525-3532, High Performance Real-Time Quantitative RT-PCR Using Lanthanide . . . .

O'Donovan, C. et al., J. Mater. Chem. 15, 2005, pp. 2946-2951, Phosphorescent oxygen-sensitive materials for biological . . . .

O'Mahony, F. et al., Environ. Sci. Technol. 39, 2005, pp. 5010-5014, Optical Oxygen Microrespirometry as a Platform for . . . .

O'Riordan, T. et al., Anal. Biochem. 278, 2000, pp. 221-227, A Cell Viability Assay Based on MOnitoring Respiration by . . . .

O'Riordan, T. et al., Anal. Chem. 74, 2002, pp. 5845-5850, Performance Evaluation of the Phosphorescent Poryphyrin Label . . . .

O'Riordan, T. et al., AJP-Regul. Integr. Comp. Physiol. 292, 2007, pp. R1613-R1620, Sensing intracellular oxygen using near . . . .

O'Sullivan, P. et al., Nucleic Acids Research 30(21), 2002, pp. 1-7, Synthesis and evaluation of phosphorescent . . . .

Padar, S. et al., Br. J. Pharmacol. 142, 2004, pp. 305-316, Differential regulation of calcium homeostasis in . . . .

Papkovskii, D. et al., Biomedical Science 1, 1990, pp. 401-407, Photodestruction in vitro of tumor cells sensitized by . . . .

Rumsey, W. et al., Science 241, 1988, pp. 1649-1651, Imaging of Phosphorescence: A Novel Method for Measuring Oxygen . . . .

Schmälzlin, E. et al., Biophysical Journal 89(2), pp. 1339-1345, An Optical Multifrequency Phase-Modulation Method Using . . . .

Subramaniam, V. et al., IEEE Journal of Selected Topics in Quantum Electronics 2(4), 1996, pp. 1107-1114, Time-Resolved . . . .

Takahashi, E. et al., Am. J. Physiol. Cell. Physiol. 291, 2006, pp. C781-C787, In vivo oxygen imaging using green fluorescent . . . .

Xue, H. et al., Anal. Chem. 76, 2004, pp. 2498-2505, Store Depletion by Caffeine/Ryanodine Activated Capacitative $Ca^{2+}$ . . . .

Chemicool.com © 2005. Definition of Phosphorescence found at: Http://www.chemicool.com/definition/phosphorescence.html.

* cited by examiner

OXYGEN SENSITIVE PROBE

This is a continuation of PCT/IE04/000031 filed Mar. 5, 2004 and published in English.

The invention relates to an oxygen sensitive probe and its use in measuring dissolved oxygen concentration in a sample.

BACKGROUND

Measurement of the dissolved oxygen concentration is an important analytical task. Measurement of the rates of oxygen uptake or release can be used for the monitoring of various chemical and biological processes. Oxygen is one of the key metabolites in living cells, tissues, organisms, sub-cellular fragments, which is continuously being consumed and/or released. Monitoring of oxygen uptake/release by particular enzymes, living cells, tissues or whole organisms can provide information about their activity, metabolic status, viability, and/or physiological response, for example as a result of the action of a drug, environmental stress, toxicant, gene or effector.

Oxygen consumption can be quantified for example by measuring pressure change in the headspace of samples placed in closed test-vials (U.S. Pat. No. 5,232,839). Dissolved oxygen concentration can be measured by electrochemical oxygen sensors such as Clark-type electrode, by gas chromatography, using paramagnetic zirconium sensors or by fluorescence quenching.

Quantitation of oxygen by luminescence quenching has a number of advantages compared to other techniques. Quenched-luminescence sensing of oxygen is usually performed using dedicated oxygen-sensitive materials based on long-decay photoluminescent dyes. Such optical oxygen probes usually comprise an oxygen-sensitive dye in an appropriate quenching medium, such as plastics. U.S. Pat. Nos. 4,003,707 and 4,810,655 describe oxygen sensing systems which employ solid-state oxygen-sensitive materials based on fluorescent pyrene butyrate and phosphorescent palladium (II)- and platinum(II)-porphyrins, respectively. Oxygen probes based on fluorescent ruthenium dyes embedded in polymers such as silicon rubber (U.S. Pat. No. 5,030,420) and Pt- and Pd-complexes of porphyrin-ketones in polystyrene and other polymers (U.S. Pat. No. 5,718,842) have also been described. Such solid-state oxygen probes are usually prepared in the form of a coating or a membrane permeable for oxygen which is brought in contact with a test sample where oxygen concentration is to be determined.

Such solid-state luminescent oxygen probes and systems based thereon have been used in various assays and applications in particular in blood gas analysis, monitoring biological activity, presence of microorganisms, cellular respiration, action of drugs, toxicants and effectors on cells, or sterility for example (WO 98/15645 and U.S. Pat. No. 5,371,016). In these assays biological samples contained living microorganisms were assessed by measuring gradients of the dissolved oxygen in a special vessel, such as sealed, vial or well of a microtiter plate. These systems suffer from the following disadvantages: limited assay flexibility due to the permanent attachment of the sensitive material to solid support, significant waste of sensing materials, particularly in applications with high sample throughput, limited possibility for the user to change the amount of sensing material and assay format used, and relatively high assay cost.

Water-soluble luminescent oxygen probes have also been described. For example, Vanderkooi et al ("An optical method for measurement of dioxygen concentration based upon quenching of phosphorescence", J. Biol. Chem., 262 (12): 5476-5482 [1987]) describe a method and apparatus for imaging of oxygen distribution in tissue using non-covalent complexes of phosphorescent meso-substituted porphyrins bound non-covalently to proteins, namely, Pd(II)-tetrakis-(4-carboxyphenyl)porphine and albumin. Similarly Vinogradov S. A. et al. (Non-invasive imaging of the distribution in oxygen in tissue in vivo using near-infrared phosphors, Biophys. J. 1996, v. 70, p. 1609-1617) describe water-soluble non-covalent complexes of Pd(II)-tetrabenzoporphyrins with serum albumin as oxygen probes for imaging. Relatively long lifetimes of these dyes result in their high sensitivity to oxygen and strong quenching in aqueous solutions. These probes are suitable for fluorescence lifetime-based detection of oxygen, however they have undefined chemical composition, and there is the possibility of binding of the dye to cells and other sample components, self-quenching of the dye and potential phototoxic action on cells.

Water-soluble phosphorescent structures on the basis of Pd-tetrakis-(4-carboxyphenyl)porphine and Pd-tetrakis-(4-carboxyphenyl)benzoporphine conjugated to multiple branched polyethyleneglycol (PEG) and polyglutamate chains have been suggested as oxygen probes (U.S. Pat. No. 5,837,865) and for cell-respirometric assays and drug screening applications (U.S. Pat. No. 6,395,555). However, such probes have complex structures (dendrimers), display heterogeneity of spectral and quenching properties, bear significant electrical charge and protonable groups. They are susceptible to various transitions and conformational changes in solutions and can also bind to sample components (e.g. albumin). All this affects spectral properties and response to oxygen of such probes (Dunphy I. et al.—Anal. Biochem., 2002, v. 310, p. 191-8; Rietveld I. B. et al, Tetrahedron, 2003, v. 59, p. 3821-3831). These probes; which emit at above 700 nm, are also difficult to measure on PMT-based fluorescence spectrometers and plate readers, which are rather insensitive in the very-near infrared spectral range.

Water-soluble fluorescent ruthenium dyes have been described for use as oxygen-sensitive probes (U.S. Pat. No. 6,306,661). These oxygen probes have much shorter emission lifetimes than the porphyrins (only few microseconds), and they are not very compatible with standard time-resolved fluorescence plate readers which typically have time resolution of above 10 microseconds. Due to polycyclic aromatic structure and relatively low molecular weight, they can be cell-permeable and toxic to the cells. The sensitivity to oxygen for these oxygen probes is not as good as for the porphyrin-based probes.

An improved and more efficient method for measuring dissolved oxygen concentration in chemical and biological processes would be very useful in a wide range of applications.

STATEMENTS OF INVENTION

According to the inventions there is provided an oxygen sensitive probe comprising a monofunctional derivative of an oxygen-sensitive photoluminescent dye covalently attached to a hydrophilic water-soluble macromolecular carrier. The dye is preferably a long-decay oxygen-sensitive phosphorescent dye.

In one embodiment, the dye has an emission lifetime in the order of 10 to 1000 microseconds in deoxygenated aqueous solution.

In another embodiment, the oxygen-sensitive photoluminescent dye comprises a single reactive chemical group for chemical conjugation to the macromolecular carrier.

In a further embodiment, the oxygen-sensitive photoluminescent dye comprises Pt(II)-porphyrin or Pd(II)-porphyrin or closely related structures.

In one embodiment, the oxygen-sensitive photoluminescent dye is selected from any one or more of Pt(II)-copropor-phyrin-I; Pt(II)-coproporphyrin-III; Pt(II)-uroporphyrin-I; Pt(II)-tetrakis(p-carboxyphenyl)porphine; Pt(II)-tetrakis(p-sulfophenyl)porphine; derivatives or analogs thereof.

In one embodiment, the oxygen-sensitive photoluminescent dye is selected from any one or more of Pt-porphyrin-ketones; Pt-benzoporphyrins; Pt-chlorins; Pd-porphyrin-ketones; Pd-benzoporphyrins; or Pd-chlorins.

In one embodiment, the oxygen-sensitive photoluminescent dye is a monofunctional p-isothyocyanatophenyl derivative of Pt-coproporphyrin-I.

In another embodiment, the oxygen-sensitive photoluminescent dye is a monofunctional amino-, maleimido- or N-succinimido-derivative of Pt-coproporphyrin-I.

In another embodiment, the macromolecular carrier comprises a polypeptide, polysaccharide, poly (ethyleneglycol).

In a further embodiment, the invention further comprises a monofunctional derivative of an oxygen-sensitive photoluminescent dye covalently attached to a monofunctional macromolecular carrier.

In one embodiment, the macromolecular carrier comprises poly(ethyleneglycol) (PEG) having molecular mass exceeding 2,000 Da.

In another embodiment, the macromolecular carrier comprises any one or more of PEG-5,000 or PEG-20,000.

In a further embodiment, the macromolecular carrier comprises PEG-20,000 with one terminal amino group.

In one embodiment, the macromolecular carrier comprises activated PEG-20,000 containing one terminal N-succinimide group.

In another embodiment, the oxygen-sensitive probe is conjugated to the terminal group(s) of a high molecular weight PEG to give predominantly a 1:1 or 2:1 conjugate.

In a further embodiment, the macromolecular carrier comprises a polypeptide having molecular weight above 5,000 dalton.

In one embodiment, the macromolecular carrier comprises albumin or immunoglobulin.

In another embodiment, the macromolecular carrier comprises dextran or amino-dextran having molecular mass exceeding 5,000 Da.

In one embodiment the macromolecular carrier and oxygen sensitive dye are present in such conjugated probe in a ratio of close to 1:1 to 1:2.

In one embodiment, the macromolecular carrier is capable of recognising and specifically binding the surface of a cell or group of cells in a sample.

In another embodiment, the invention provides an oxygen sensitive probe as defined above in combination with another probe, especially a fluorescent bioprobe.

In another aspect, the invention provides a process for preparing an oxygen probe comprising reacting functionalised derivatives of an oxygen-sensitive photoluminescent dye and/or water soluble macromolecular carrier to form a stable chemical linkage.

In a further embodiment, the dye is conjugated to the macromolecular carrier at a specific site(s).

In one embodiment, the dye is reacted with the carrier in a single step.

In another aspect, the invention provides a method for monitoring oxygen uptake by chemical or biological samples comprising the step of adding an oxygen sensitive probe to a test sample and measuring changes in the probe emission which reflect changes in the dissolved oxygen concentration, wherein the probe comprises a monofunctional derivative of an oxygen-sensitive photoluminescent dye covalently attached to a water-soluble hydrophilic macromolecular carrier. The probe is preferably a probe as defined above.

The biological sample may contain cells, microorganisms, subcellular organells, animal tissue or aquatic animals.

In one embodiment, prior to or after addition of the oxygen probe the sample is treated with a drug, hormone, or other effectors.

In another embodiment, the method determines the number of cells, cell viability, drug or effector action on cells in a sample.

The sample may contain an oxygen dependent enzyme or enzymatic system and corresponding substrate(s). The method may be used for determining the concentration of enzyme substrate, or the rate of metabolism of this substrate. The method may be used for determining enzyme activity or inhibition.

In a further embodiment, the luminescent intensity of the oxygen probe is monitored and used to determine changes in oxygen concentration.

In one embodiment, the luminescent signal of the oxygen probe is measured by time-resolved fluorescence with microsecond time resolution.

In another embodiment, the delay and gate times are comparable with the lifetime of the oxygen probe in an air-saturated sample.

In a further embodiment, time-resolved measurements of the oxygen probe are carried out at several delay and/or gate times after excitation.

In one embodiment, the probe response to oxygen is optimised by optimising the parameters of time-resolved fluorescence measurement, namely the delay and/or gate time.

In another embodiment, the luminescent signal of the oxygen probe is measured using phase-modulation technique.

In a further embodiment, excitation of the oxygen probe is performed by a laser compatible with the oxygen probe.

The sample and the emission of oxygen probe may be analysed with a fluorescence imaging system.

In one embodiment the process includes the step of sealing the sample. The sample may be sealed by covering the sample with a liquid seal material. The liquid seal may comprise mineral oil. Mineral oil reduces diffusion of ambient air oxygen into the sample thus acting as a seal.

BRIEF DESCRIPTION OF THE DRAWINGS

The invention will be more clearly understood from the following description thereof, given by way of example only, with reference to the accompanying drawings, in which.

DETAILED DESCRIPTION

The invention provides an oxygen-sensitive probe comprising a conjugate of a monofunctional oxygen-sensitive photoluminescent dye such as a phosphorescent porphyrin dye and a hydrophilic water soluble macromolecular carrier. The oxygen sensitive probe is produced by covalent attachment of a monofunctional derivative of an oxygen-sensitive photoluminescent dye to specific sites on a specially selected macromolecular carrier to form a stable chemical bond(s) between the two species. Preferably the macromolecular carrier is also monofunctional. The one to one conjugate provides an optimal oxygen sensitive probe which has a defined chemical structure and attachment site.

Oxygen probes on the basis of unconjugated dyes have low molecular weight, considerable hydrophobicity, tendency to interact with sample components and cytotoxicity. Their luminescent properties usually depend strongly on probe concentration sample composition and assay conditions. Polysubstituted oxygen probes have improved solubility properties and inertness. However, the attachment of several carrier moieties to one luminophoric moiety allows multiple conformations and variable microenvironment in the vicinity of the dye, thus engaging the dye in numerous weak interactions, proximity quenching and other effects. Since the long-decay photoluminescent dyes are generally very sensitive to microenvironment, such poly-substituted conjugated oxygen probes still display complex photophysical behaviour, e.g. sensitivity to pH, medium and sample components.

In the mono-substituted oxygen probes of the invention these undesirable effects such as dye-carrier interactions, multiple conformations, proximity quenching and solvent effects, are minimised by having only one carrier moiety attached to the dye via a specific site and linkage. This results in more simple and reproducible photophysical and oxygen sensing properties of the probe.

The oxygen sensitive probes of the invention are used for measurement of dissolved oxygen concentration in biological and chemical assays, particularly cell-based screening assays and related applications. The probes are designed and optimised with respect to their structural, physicochemical and spectral characteristics, optimal signal response to oxygen within the ambient oxygen range, biocompatibility and other practical considerations. The oxygen probes provide optimal performance in cell-respirometric assays based on the monitoring of the rates of uptake or release of dissolved oxygen.

The preferred oxygen probes of the invention are those in which the luminescent dye is conjugated to the carrier macromolecule at specific sites on the carrier macromolecule, for example, at the end(s) of the polymeric chain. In this way, one can achieve a well-defined structure for the conjugate, ideally 1:1, microenvironment of the dye, and thus ensure predictable photophysical properties, sensitivity to oxygen and reproducible synthesis of batches of the oxygen probe.

The optimised oxygen probe displays a number of improvements over previously described oxygen probes. These new properties are particularly advantageous for chemical and biological screening assays based on measurement of the rates of oxygen uptake or release by multiple samples, particularly samples containing living cells, sub-cellular components, oxygen-dependent enzymes, enzymatic systems, tissues or whole organism(s).

Synthesis of such oxygen probes is preferably carried out in one step using functionalised derivative(s) of the dye and macromolecule, which can spontaneously react with each other to form covalent conjugates with stable chemical linkage. Examples of such functional groups that may be used for conjugation include amino, carboxy, hydroxy, SH- and aldehyde groups. Other examples are reactive chemical groups such as N-succinimide, maleimide, isothiocyanatophenyl, sulfonylchloride or chloroanhydride which can spontaneously react with other groups such as amino-, —SH, —OH groups. The chemical groups are introduced to the dye and macromolecular carrier by standard chemical means to produce the corresponding derivatives.

The preferred synthesis routes are those in which the dye and the carrier are conjugated to each other in a single step without the use of additional chemical reagents. This is usually carried out by mixing the two components in certain ratios in a suitable solvent and incubating over reasonable period of time to allow conjugation to occur. Reactive derivatives of the dye spontaneously react with functional groups present on the macromolecule, or vice versa. The conjugate formed is then isolated from the reaction mixture using appropriate purification techniques such as chromatography or fractionation. This results in a pure conjugated oxygen probe of known chemical composition, photophysical and sensing properties.

It is advantageous for the dye to be sufficiently hydrophilic and water-soluble, as some macromolecules such as proteins do not all withstand conjugation in organic solvents. In these cases conjugation with macromolecules can be carried out in aqueous solutions. Non-specific interactions of the conjugates with sample components are minimised in the case of hydrophilic dyes and carriers.

The preferred luminescent dyes of the invention are monofunctional derivatives of the phosphorescent Pt(II)-porphyrins, as well as related structures such as Pt(II)-porphyrinketones, Pt(II)-benzochlorins, Pt(II)-chlorins. Pd(II)-complexes of porphyrins, chlorins and some other related structures also can be used in the probes. All these dyes are known to be moderately quenched by ambient oxygen in aqueous solutions, have sufficiently long emission lifetimes, favourable spectral characteristics for biological applications and can be used in this invention for conjugation to macromolecules and in cell-respirometric assays.

Monofunctional derivatives of water-soluble Pt-coproporphyrins are preferred dyes. They are easily conjugated to macromolecules under mild conditions and with high yields, for example via primary amino or SH-groups of the carrier macromolecule. Preferred dyes include mono p-isothiocyanatophenyl, N-succinimide, maleimide and amino derivatives of Pt-coproporphyrin-I and Pt-coproporphyrin-III in tri-acid or trialkyl ester form, which can react with various chemical and biological molecules bearing, respectively, free amino, —SH and N-succinimide groups to form stable chemical linkage. Some particular examples of these dyes and conjugation procedures are described in PCT/FI99/00898. Oxygen probes based on Pt-coproporphyrins have emission at about 650 nm and they are suitable for time-resolved fluorescence measurements and lifetime-based oxygen sensing with relatively simple instrumentation. Due to their high spectral sensitivity and selectivity, the probes can be used in trace amounts even in complex biological samples with high scattering and autofluorescence.

Other dyes closely related to Pt-coproporphyrins may also be used such as monofunctional derivatives of Pd-coproporphyrin, Pt-tetrakis(p-carboxyphenyl)porphine, Pt-coproporphyrin-ketones and Pt-chlorins-e6. These derivatives, however, emit at longer wavelengths (around 700 nm).

Conjugation of the above oxygen-sensitive luminescent dyes to a hydrophilic macromolecular carrier provide improved oxygen probes which can monitor low levels of oxygen uptake or release by test samples in a convenient way and on a micro-scale.

The preferred oxygen probes of the invention are conjugates of Pt-porphyrins with poly(ethyleneglycols), (PEGs), such as PEG-5,000, PEG-10,000 and PEG-20,000 (numbers correspond to different molecular weights). PEG molecules normally contain terminal OH-group(s), and no other reactive functionality within the chain. These terminal OH-groups are suitable for chemical modification and/or for site-directed conjugation with the oxygen-sensitive dyes. Functionalised PEG derivatives such as mono-and di-substituted amino-PEG, N-succinimide-PEG, aldehyde-PEG, are also easily available. For such carriers mono-and di-substituted conjugates with Pt-porphyrins can be synthesized, which have well-defined chemical structures, physicochemical and optical properties.

The invention also provides oxygen probes based on protein conjugates with Pt-porphyrins. It was found that photophysical properties and sensitivity to oxygen for such oxygen probes is largely dependent on the conjugate composition, particularly the degree of labelling of protein with the dye. The conjugates with a low degree of labelling are more sensitive to small changes in oxygen within ambient (air-saturated) oxygen range and they also give stronger specific emission signals. The conjugates having dye:protein ratio close to 1:1-1:2 are preferred over conjugates with a high degree of substitution when multiple dye molecules are attached to each protein molecule. Due to multiple sites for the attachment of dye available in proteins such as multiple amino, carboxy, OH groups, the chemical composition of such conjugates is not as well defined as for the PEG conjugates. Such oxygen probes are more difficult to make in reproducible batches and standardise. Furthermore, protein conjugates can be gradually ingested and degraded by the cells or the sample components (proteases), especially in prolonged experiments with biological samples, and on long term storage in solutions. Nevertheless, oxygen probes based on protein conjugates have been found to provide reasonably good performance with respect to oxygen sensing in solutions and also suitable for cell respirometric assays.

The invention also provides oxygen probes based on Pt-porphyrins conjugated to polysaccharides such as dextrans. Dextrans are more stable to biodegradation than proteins, they are water-soluble, inert and available in various molecular weights. Dextrans contain multiple hydroxy groups which are suitable for the attachment of the phosphorescent dye either directly or using modified dextrans with specially introduced chemical groups such as amino, aldehyde or diethylaminoethyl groups. Dextran conjugates with various fluorescent dyes have been described and used as cell-impermeable probes (R. P. Haugland, Handbook of Fluorescent Probes and Research Chemicals, 6$^{th}$ Edn., 1996, Molecular Probes).

We have found that conjugates of monofunctional Pt-porphyrins and dextrans may also be used as water-soluble oxygen probes. Oxygen probes based on relatively high-molecular weight (above 5,000 Da) dextrans are cell-impermeable and are more stable to biodegradation than protein conjugates. Although modification and conjugation to dextrans is usually random and the exact site of the dye attachment to this carrier can not be easily defined or controlled, the number of functional groups in dextrans available for conjugation with Pt-porphyrins can be kept relatively small, for example, 2-6 amino groups per mole in amino-dextrans. Dextrans consist of uniform fragments (sugar blocks) and their conformation which determines the dye microenvironment is not so variable as for proteins, which provide them with more stable photophysical properties. The sensitivity of dextran conjugates to oxygen is similar to the PEG conjugates, however their emission is lower due to internal quenching of the dye by dextran. Oxygen probes based on dextran conjugates are quenched by oxygen in air-saturated solutions and give good response to changes of oxygen concentration.

It was surprisingly found that the response of a conjugated oxygen probe to oxygen is dependent on the nature of the carrier rather than on its size (molecular weight) and conjugation chemistry. Oxygen sensitivity of PEG-5,000 and PEG-20,000 conjugates is similar, so too is the sensitivity of BSA and IgG conjugates, despite the significant difference in molecular weight and size. At the same time, Pt-coproporphyrin-PEG conjugates are more sensitive to oxygen than corresponding dextran and protein conjugates. As opposed to protein and dextran conjugates, interaction of the Pt-porphyrin dye with the carrier macromolecule is practically absent in PEG conjugates (emission yield and lifetime are essentially unaffected), which is a significant advantage. Emission lifetime for the PEG and dextran conjugates in air-saturated solutions (starting point of all cell-respirometric assays) appear to be shorter than 20 μs. For some time-resolved luminescent plate readers, this lifetime can result in the loss of the probe signal (delay times for many plate readers is often above 20 μs). In such cases, the BSA conjugates can be more suitable for use, as they can provide higher signals or may be used at lower concentrations than PEG or dextran conjugates. Therefore, by selecting the macromolecular carrier for the dye, it is possible to optimise the probes' response to oxygen, its sensitivity and compatibility with a measurement device.

The oxygen probes of the invention show a number of advantages over other known oxygen probes. The hydrophilic macromolecular carrier provides the oxygen probe with improved water-solubility. Carboxylic metalloporphyrins as well as many other even more hydrophobic dyes, which tend to aggregate or are even insoluble in aqueous solutions, can be solubilised and kept in monomeric water-soluble form when conjugated to hydrophilic macromolecules such as proteins, polysaccharides or synthetic polymers. Interactions of the oxygen probe with sample components such as binding to proteins, lipids, cells or non-specific adsorption on surfaces are reduced with the conjugated bio-reagents of the invention. Self-quenching, which is a known limitation for oxygen-probes based on the free or unconjugated dye is also significantly reduced. Overall, spectral properties and the response to oxygen concentration changes become more stable, predictable and less dependent on the sample contents using the conjugated oxygen probes of tie invention compared to the free dye. The large size of the probe also minimises its penetration or transport into the cells. The conjugates of the invention, in particular the 1:1 conjugates, provide more homogeneous, stable and reproducible photophysical and sensing properties than other known water-soluble oxygen probes.

The oxygen probes of the invention have a further advantage. The oxygen probe is able to bind to the surface of test cells. Since oxygen is consumed inside cells, oxygen gradients are initially created in the vicinity of a cell and then propagate further in solution Therefore an oxygen probe which is brought in close proximity to the cells is more sensitive to oxygen uptake by the cells, than a probe which is uniformly distributed in a sample solution. We have found that binding of the conjugated oxygen probes to cells and/or surfaces has minor impact on their signal and their sensitivity to dissolved oxygen in samples. An example of such an oxygen probe includes antibodies to particular cell surface receptors labelled with Pt-porphyrins. Addition of the probe to a sample solution containing cells results in the preferential binding of the probe to the cells.

The measurement of oxygen uptake by biological and chemical samples using the oxygen probes of the invention may be carried out by a number of conventional methods. In one methods a plurality of test samples are placed in a dedicated assay substrate together with an oxygen probe of the invention. The signal from the oxygen probe in each sample is monitored on a fluorescence plate reader, spectrometer or imager, to establish oxygen gradients in each sample on the basis of changes in the probe luminescence.

The method is applicable to various assay substrates such as standard 24-, 96-, 384- or 1568-well plates or similar devices. Dedicated microchamber devices, microfluidic systems or customised devices specially designed and optimised for cell-respirometric assays may also be used.

The oxygen probe may be pre-mixed with the sample which is then added to the assay substrate, or it may be added directly to the microwells or microchambers or assay buffer.

The working concentration of the oxygen probe is optimised according to assay specifications and practical requirements. Quenched-luminescence oxygen sensing is essentially independent of the probe concentration, due to its physical rather than chemical principle (collisional quenching). However, the sensitivity of the measurement device and its time-resolution (if any), as well as sample optical properties, measurement geometry or properties of assay substrate, also need to be taken into account. The working probe concentration should be large enough, so that its luminescent signal under the assay conditions is easily distinguishable from background signal (scattering and autofluorescence). At the same time, it is desirable to keep working probe concentrations low in order to minimise the waste and assay costs, especially for high throughput screening. The working probe concentration is typically optimised in a separate simple experiment, by making several different dilutions of the probe stock and measuring them on the assay set-up.

Time-resolved fluorescence (TRF) detection is the preferred method of detection. TRF may be carried out on time-resolved fluorescence plate readers equipped with a pulsed flashlamp (e.g. Xe-flashlamp) or laser (e.g. 532 nm laser). TRF typically provides better sensitivity with low background and high signal-to-noise ratio for the oxygen probes of the invention. TRF may also be carried out at very low concentrations of the oxygen probe. TRF is particularly advantageous for biological samples with high scattering and autofluorescence, such as samples containing cells, high protein content or pigments. Red emission of the oxygen probes based on Pt-porphyrins (~650 nm) and relatively long phosphorescence lifetimes (ranging between 10 and 100 microseconds) make them very compatible with existing fluorescence plate readers and spectrometers with microsecond time resolution. Using these devices very low (subnanomolar) concentrations of the oxygen probes can be easily detected and therefore used in cell-respirometric assays.

Compared to other oxygen probes, those of the invention may be used at lower working concentrations in cell-respirometric assays and related applications. Conventional (prompt) fluorescence readers and spectrometers may also be used with the oxygen probes. These devices usually require higher working concentration of the bio-reagent than time-resolved fluorometers, however they also provide satisfactory performance in cell-respirometric assays.

TRF detection allows for lifetime-based oxygen sensing using the oxygen probes. For example, by measuring the probe intensity signal at several gate times after excitation. Such measurements give an estimate of the probe lifetime which is also dependent on the oxygen concentration and can be used for oxygen quantitation. Lifetime-based oxygen sensing in some cases may be more advantageous than intensity based sensing, as it has more a stable calibration and allows internal referencing and compensation for the probe bleaching, static quenching, variation of sample optical properties, probe concentration and measurement geometry. All these factors have minor impact on the lifetime measurements, but they may be significant for intensity measurements. Indirect lifetime based oxygen sensing may also be carried out using the oxygen probes and method of the invention in conjunction with phase-modulation techniques, i.e. by phase measurements.

TRF measurements can also be used to tune the probe sensitivity and response to oxygen concentration changes, by varying the measurement parameters such as the delay time and gate time. The amplitude of the probe signal change in the air-saturated solutions is generally higher in time-resolved mode than in prompt fluorescence mode. As the delay time increases and the gate time is kept constant, the amplitude of signal change increases even further. Therefore, time-resolved fluorescence detection potentially allows for more sensitive measurements of oxygen concentration changes.

The measurement of the probe emission in test samples during an assay may be carried out continuously by monitoring samples one by one sequentially or simultaneously on a multi-channel device or imager. Typically samples are scanned periodically at certain intervals over a reasonable period of time sufficient to establish the basis of several measurement changes in luminescent signal and determine oxygen gradients in each sample. Since cell-respirometric assays are usually started in air-saturated conditions, end-point detection may be used in certain cases.

Quantitation of the absolute rates of oxygen uptake and oxygen concentration in test samples is usually not necessary. In most cases appropriate standards or control experiments are incorporated in the assay or carried out separately and are used as references. In this case, measured time profiles of luminescent signal which reflect oxygen gradients in the sample are used for the assessment of the sample metabolic activity. Initial slopes of fluorescent signal are commonly used to compare the activity of samples between each other and a standard.

The samples undergoing examination by oxygen sensing usually comprise live cells. The cells may be treated with drugs, effectors prior to the assay or during the assay, to determine the effects on the cells. Control samples which contain untreated cells are typically incorporated in the assay and used as a reference. The samples may also comprise oxygen-dependent enzymes, enzymatic systems, cellular extracts, sub-cellular fragments, tissues and whole organisms.

The assay may also be used to determine the number of cells in test samples, their rate of proliferation, metabolic status or viability, on the basis of the rates of oxygen uptake by test samples. The assay may also be used to measure activity and inhibition of a variety of oxygen-dependent enzymes and enzymatic systems, or to measure concentration of substrates of such enzymes and the rates of their metabolism.

Overall, the oxygen probes of the invention in particular conjugated monofunctional Pt-porphyrins offer many advantages over existing systems. They provide oxygen probes with well-defined chemical composition, photophysical and oxygen sensing properties which provide predictable and highly reproducible luminescent responses to oxygen concentration in biological samples, and changes as a result of oxygen uptake-release by these samples. The probes are also highly water-soluble, cell-impermeable and have low cyto and phototoxicity. They are also stable to biodegradation.

The oxygen probes provide optimal response to oxygen which results in moderate (1.5-15-fold) quenching of the probes in air-saturated conditions. Such moderate quenching and optimal spectral and lifetime properties allow sensitive detection of the oxygen probes on many conventionally used fluorescence spectrometers and commercial plate readers. The probes may be used in trace quantities in cell-respirometric micro-assays and provide good performance, versatility and multiple applications. The quenching eliminates as the sample dissolved oxygen gets consumed by the sample and the probe responds to this by increasing its luminescence intensity and lifetime.

The oxygen probes of the invention provide high sensitivity, versatility, flexibility and high sample throughput. The oxygen probes also allow miniaturisation of assays and reduce overall assay costs. In addition and importantly the oxygen probes are compatible with standard equipment such as microplates, fluorescence plate readers, robotic and liquid handling equipment. The oxygen probes of the invention are better and more convenient for use than other oxygen probes described to date. They are suitable for a variety of different biological and chemical assays particularly cell-based micro-assays and drug screening applications.

The oxygen probes are particularly suitable for use with sensitive biological samples containing enzymes, living cells, cellular fragments, tissues or whole organisms. They are essentially inert and friendly with respect to the samples and can be used in conjunction with various assay substrates such as microtiter plates, tubes, sealed low-volume platforms, microfluidic systems and customised measurement set-ups, as well as with standard liquid handling and measurement equipment such as fluorescence and time-resolved fluorescent (TRF) plate readers and imagers. The oxygen probes may be used at trace concentrations to monitor the concentration of the dissolved oxygen in samples and its changes.

Since the oxygen probes have very distinct spectral and lifetime characteristics and are used in minute quantities, they can be detected with high selectivity in the presence of other fluorophores and probes present in or added to the sample. They therefore enable to combine oxygen measurements with measurement of other parameters within the same sample, in parallel or sequentially. For example, measurement of cellular DNA content, intracellular calcium, pH, ions, membrane potential, etc. with corresponding probes provides additional information and added value about test samples. These probes can be combined with the oxygen probes to allow multiplexed cell-based assays.

The invention is illustrated by the following non-limiting examples.

EXAMPLE 1

Synthesis of Oxygen Probes Based on Monofunctional Isothiocyanatophenyl Derivative of Platinum(II)-coproporphyrin and Proteins A sample of p-isothiocyanatophenyl-derivative of platinum(II)-coproporphyrin (PtCP-NCS) was dissolved in dimethylsulphoxide (DMSO) at a concentration of 5 mg/ml ($4.95 \times 10^{-3}$M). 50 ul of this solution was added to 950 ul of serum albumin in 0.05 M carbonate buffer, pH 9.6 (1.7 mg/ml, $2.55 \times 10^{-5}$M) and the resulting reaction mixture was incubated at room temperature in dark place. 200 ul aliquots of this solution were taken at specific time intervals (5 min, 10 min, 30 min, 1 h, 3 h) and separated on a gel-filtration column (Sephadex G-25) equilibrated with phosphate buffer saline, pH 7.4, collecting fractions of the conjugate peak. Thus, conjugates with different degrees of labelling with PtCP were obtained, their concentration and degree of labelling were determined based on their absorbance at 280 nm and 380 nm.

EXAMPLE 2

Synthesis of Oxygen Probes Based on Monofunctional Isothiocyanatophenyl Derivative of Pt-coproporphyrin and Dextrans Conjugation of PtCP-NCS with dextran was carried out as in example 1, using 3 mg/ml solution of amino-dextran-40,000 containing 8.1 moles of amino groups. Conjugates containing different number of dye molecules attached to a dextran carrier were obtained.

EXAMPLE 3

Synthesis of Oxygen Probes Based on Monofunctional Isothiocyanatophenyl Derivative of Pt-coproporphyrin and Mono-amino PEG PtCP-NCS was dissolved in DMSO at a concentration of 5 mg/ml ($4.95 \times 10^{-3}$M). 100 ul of this solution was added to 900 ul of CH3O—POE-NH—CO—C2H4-NH2(M.W. 5,000 or 20,000) in 0.05 M carbonate buffer, pH 9.6 (1.7 mg/ml, $2.55 \times 10^{-5}$M) and the resulting reaction mixture was incubated at room temperature for 2 hours in dark place and then separated on a Sephadex G-25 desalting column equilibrated with phosphate buffer, pH 7.4. Fractions of the PEG-PtCP conjugate were collected, desalted and freeze dried for long-term storage.

EXAMPLE 4

Oxygen Probes Based on Monofunctional Activated PEG and Mono-amino-derivative of Pt-coproporphyrin PtCP-mono-NH2 derivative was dissolved in DMSO at a concentration of 5 mg/ml ($4.95 \times 10^{-3}$M). 100 ul of this solution was added to 900 ul a solution of CH3O-PEG-N-succinimide (M.W. 20,000) in chloroform (5 mg/ml) and incubated at room temperature for 2 hours in dark place. 10 ml of ether were then added to the reaction mixture. Precipitated PEG-PtCP conjugate was separated by centrifugation and the supernatant containing unbound PtCP was discarded. The conjugate was re-dissolved in a minimal amount of chloroform and the precipitation procedure was repeated four times and then the conjugate was dried. Pure PEG-PtCP conjugate was stored at −20° C.

EXAMPLE 5

Comparison of Photophysical and Sensing Properties of the Oxygen Probes Described in Examples 1-4

All the above oxygen probes based on PtCP dye have strong absorption in spectral regions 360-400 nm (maximum at 380 nm) or 525-545 nm (maximum at 535 nm), which can be used for excitation. Spectral characteristics of the oxygen probes are close to those of the free PtCP (well described in literature). These oxygen probes are excitable with 532 nm lasers, which can be used in continuous wave or in pulsed mode, and with xenon flash lamp. The probes are suitable both for prompt (steady-state) and time-resolved phosphorescence measurements and allow intensity-based and lifetime-based sensing of oxygen.

All the oxygen probes described above in examples 1-4 displayed good solubility in aqueous solutions within a broad range of pH and ionic strengths and buffer composition. They can be stored in dry form and in solution for prolonged periods of time, without any detectable changes in their spectroscopic and oxygen sensing properties.

The response of the probes to oxygen was tested by measuring their luminescence in aqueous solutions equilibrated with different concentrations of dissolved oxygen by bubbling standard oxygen-nitrogen gas mixtures. When changing from air-saturated to deoxygenated aqueous solution, the probes showed approximately 1.8-20 fold enhancement of the phosphorescence intensity, which was fully reversible and independent of the probe concentration. Measurement in time-resolved mode usually produced higher signal change.

Figure 1:
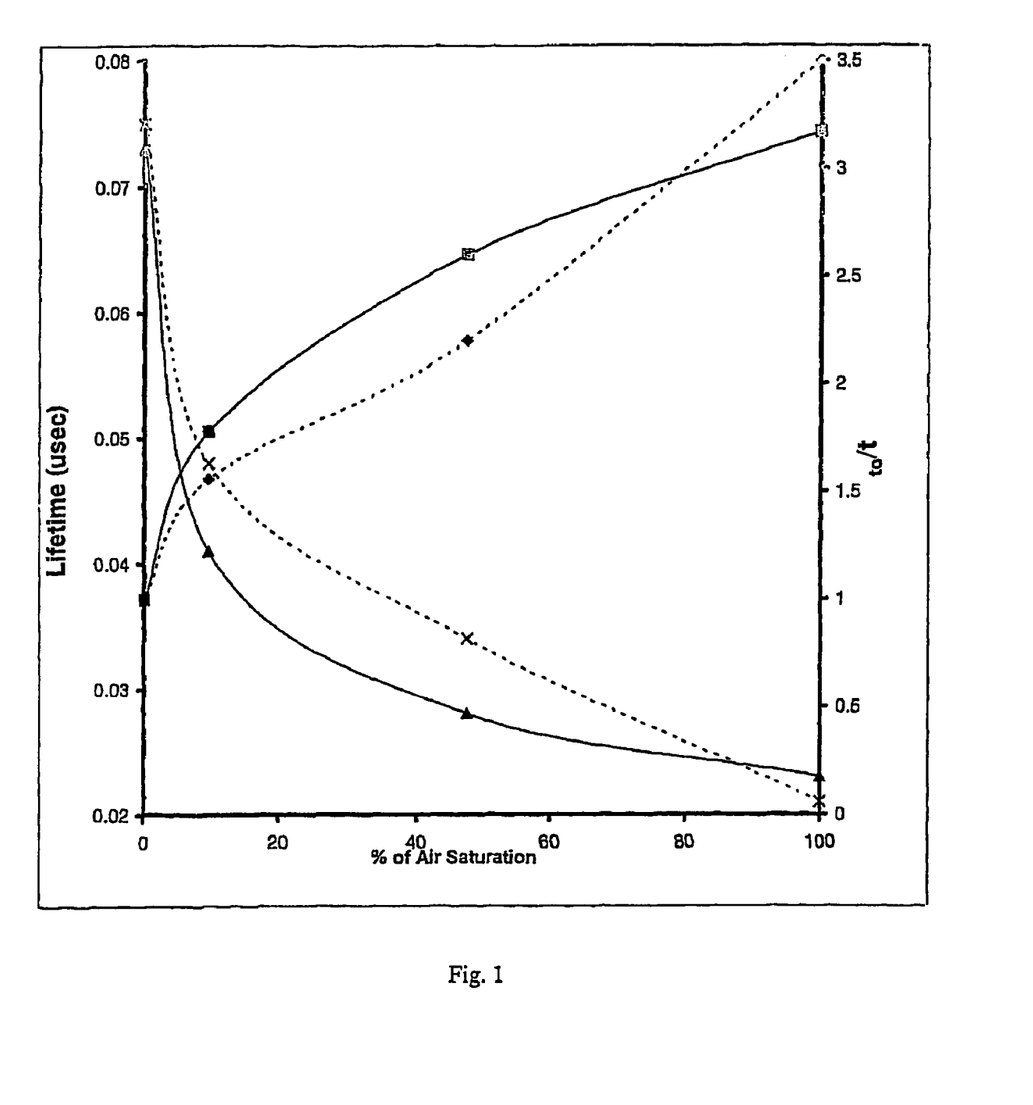
FIG. 1 is a graph showing the response (lifetime $\tau$ and $\tau_0/\tau$) of two PtCP-BSA conjugates to changes in the dissolved oxygen concentration (% of air saturation): solid lines—10:1 conjugate ($=\tau$, $=\tau_0/\tau$); dashed lines—2:1 conjugate (x=$\tau$, =$\tau_0/\tau$), 22° C., in PBS, pH 7.4.
Figure 2:
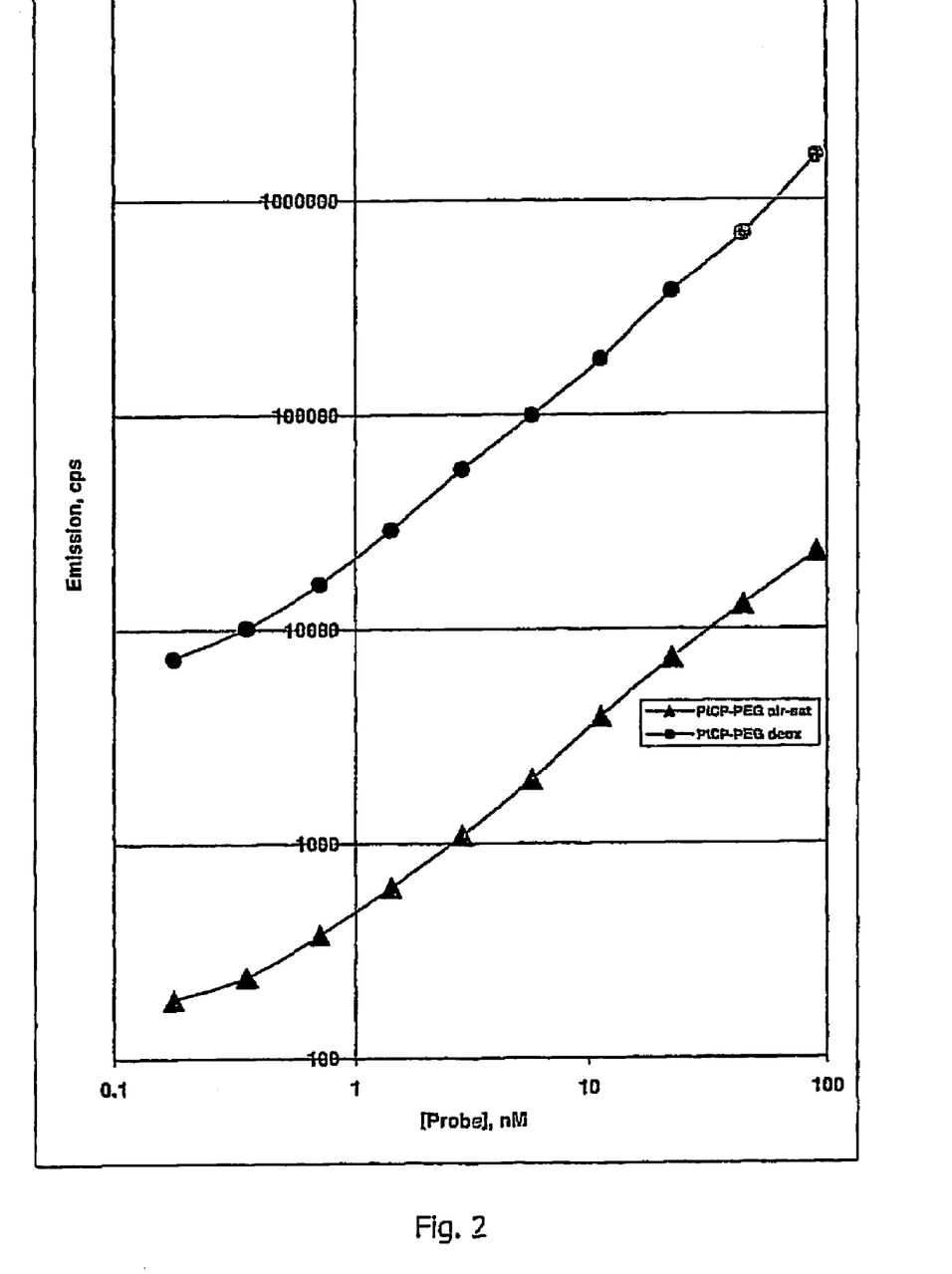
FIG. 2 is a graph showing the phosphorescent signals of PtCP-BSA (2:1) oxygen probe in a 96-well plate on a Victor® plate reader in time-resolved mode (filters 340/642 nm, delay time 30 us, gate time 80 us), measured at different concentrations in air-saturated (bottom curve) and in deoxygenated (top curve) buffer (PBS, pH 7.4, 23° C./)

Oxygen calibration functions of selected PtCP-BSA conjugates presented in FIG. 2. One can see that the Stern-Volmer quenching plots for PtCP-BSA conjugates with low degree of substitution (2:1) were seen to be close to linear, while for highly substituted conjugates, significant deviation from linearity was observed. In conditions close to air-saturated, which is the starting point of cell-respirometric assays, the probe sensitivity to minor changes in oxygen concentration was higher for the conjugates with low degree of substitution—see the right part of the curves in FIG. 1. The sensitivity, expressed as the slope of the calibration curve at air-saturated oxygen concentrations (100% of air saturation), was 0.25 us and 0.10 us per % of air saturation, respectively. A higher degree of substitution had a significant impact on the emission yield of PtCP label, which tended to decrease significantly, though the overall emission of the conjugates still increased (Table 1). Therefore, the sensitivity to oxygen of this type of the probe can be optimised by varying the composition of this conjugate. The conjugates containing 1-3 molecules of PtCP per BSA molecule appear more suitable for oxygen sensing and cell-respirometric assays than conjugates with a higher degree of labelling.

The emission lifetimes of the PtCP-BSA probes change from about 25 us in air-saturated solutions to about 60-70 us in deoxygenated solutions. Such relatively long emission lifetimes of the probes both in air-saturated and deoxygenated solutions make them compatible with commercial time-resolved fluorescence plate readers, thereby allowing time-resolved detection and phosphorescence lifetime based oxygen sensing. The ArcDia plate reader, which was custom-designed for sensitive detection of PtCP label, was found to be ideally suited to time-resolved measurements with the PtCP-BSA oxygen probes and for cell respirometry.

A general comparison of the oxygen probes based on protein, dextran and PEG conjugates of Pt-coproporphyrin synthesised according to Examples 1-4 is given in Table 1 below.

One can see that internal quenching in PEG conjugates is the smallest (largest $\tau_0$ and $I_0$), and that they are more sensitive to oxygen than the other two types of probes.

TABLE 1

Phosphorescent and quenching characteristics of different oxygen probes.

| Oxygen probe (dye:carrier ratio) | I | $I_0$ | $I_0/I$ | $\tau$ (μsec) | $\tau_0$ (μsec) | $\tau_0/\tau$ |
|---|---|---|---|---|---|---|
| PtCP-BSA (0.9:1), Example 1 | 110 | 332 | 3.0 | 26.9 | 72 | 2.6 |
| PtCP-BSA (2.6:1) Example 1 | 118 | 448 | 3.8 | 26.2 | 67 | 2.36 |
| PtCP-BSA (7.5:1) Example 1 | 134 | 696 | 5.1 | 24.5 | 60 | 2.45 |
| PtCP-dextran (1:1), Example 2 | 9 | 123 | 13 | 12 | 85 | 7.1 |
| PtCP-dextran (3:1), Example 2 | 29 | 297 | 10.3 | 12 | 85 | 7.1 |
| PtCP-dextran (8:1), Example 2 | 71 | 748 | 10.7 | 12 | 85 | 7.1 |
| PtCP-PEG-5 (1:1), Example 3 | 34 | 610 | 17.9 | 13 | 100 | 7.7 |
| PtCP-PEG-20 (1:1), Example 4 | 29 | 527 | 18.1 | 13 | 100 | 7.7 |

Note:
$\tau$, $\tau_0$ and I, $I_0$ - emission lifetimes and intensities in air-saturated and deoxygenated solution, respectively. Conditions: phosphate buffer saline, pH 7.4, 25 °C.

A number of modern multilabel readers, such as the Victor® family (PerkinElmer Life Sciences) and alike, which operate with Xe-flashlamp and have minimal time resolution of 20-30 us or less, are suitable for time-resolved measurements with PtCP-BSA oxygen probes, provided that the appropriate PMTs and excitation and emission filters are installed. Sensitivity of the probe detection on standard plate readers was determined. Two rows of identical serial dilutions of the PtCP-BSA and PtCP-PEG oxygen probes (synthesised according to Examples 1 and 4) were made in the wells of standard 96-well plates, using the probe stock (~1 μM), 1:3 dilution step and final volume of 200 μl. The first set of wells contained phosphate buffer saline, pH 7.4 (air-saturated solution), while the second contained the same buffer with additional 50 mM of $Na_2SO_3$ (deoxygenated buffer). The microplate containing these samples was then measured on a Victor2 fluorescence plate reader (Perkin Elmer Life Sciences) using a set of filters 340/642 nm, delay time 30 us and gate time 90 us. The results shown in FIG. 2 (PtCP-PEG-20,000) demonstrate that the oxygen probes are detectable within a broad range of concentrations, from about 0.1 nM upwards. They can be used in cell-respirometric assays (working concentration can be optimised for particular instrument and application), their response to oxygen (i.e. relative signal change) is easily detected and it is practically independent on the probe concentration. Pt-porphyrin based oxygen probes provided low dark counts, high signal-to-noise ratio and almost 2-40-fold signal increase when oxygen concentration changes from air-saturated and deoxygenated solution. They can be used within a broad range or working concentrations from about 0.1 nM upwards.

We have shown that changes in the buffer pH (pH 5.0-8.5), the use of protein additives (serum) have very minor, if any, impact on the probe phosphorescence and its response to oxygen concentration changes. A variety of common media used for culturing cells can be used with the probes in respirometric assays (see examples below). Although the presence of chromophoric substances in the medium or sample (e.g. phenol red pH-indicator) may reduce the probe signal due to inner filter effect, the probes still can be used to monitor changes in oxygen concentration (though more probe might be required).

Similar results with the oxygen probes were obtained with the time-resolved fluorescence plate reader, which employed 10 mW 532 nm laser pulsed at 1 kHz frequency, 650 nm emission filter, photon counting detector. Measurement parameters were: pulse duration—10 us, delay time—20 us, gate time—90 us. Furthermore, it was shown, that by measuring the oxygen probe signal at different delay time, e.g. at 0, 10 us and 20 us, one can adjust the response of the probe to oxygen (i.e. Io/I ratio) and, hence, the probe sensitivity in cell-respirometric assays. Changes of the quenched-phosphorescence intensity of PtCP-BSA and PtCP-PEG-20,000 oxygen probes as a function of delay time measured at constant gate time (70 us) are shown in Table 2. One can see, that at longer delay times the oxygen probes produce greater signal response to changes in the dissolved oxygen concentration (i.e. relative signals Io/I). However, in this case their absolute signals also decrease significantly, so that more probe is needed for the assay to produce sufficient signal which is easy to measure. Time-resolved fluorescence mode provides essentially background-free conditions for the detection of the oxygen probes of this invention.

TABLE 2

Measured time-resolved phosphorescent signals and response to oxygen as function of delay time for the PtCP-PEG-20,000 and PtCP-BSA probes (12.5 nM in PBS, 22° C.) measured on a time-resolved plate reader (Exc/Em - 532/650 nm).

| | PtCP-PEG (1:1) | | | PtCP-BSA (1:1) | | |
|---|---|---|---|---|---|---|
| Delay time, us | I air (cps) | Io (cps) | Io/I | I air (cps) | Io (cps) | Io/I |
| 0 (prompt fluor) | 17100 | 179500 | 10.5 | 37100 | 69500 | 1.8 |
| 10 | 4865 | 133700 | 27.5 | 13570 | 40170 | 2.9 |
| 20 | 2832 | 108100 | 38.2 | 8680 | 32900 | 3.7 |

In contrast, oxygen probes on the basis of ruthenium(II) complexes, having lifetimes of only a few microseconds and less, are not suitable for time-resolved measurements on most of commercial time resolved fluorescence plate readers.

At the same time, the oxygen probes of the invention also can be measured on conventional (prompt) fluorescence spectrometers and plate readers. On the other hand, time-resolved fluorescence detection usually provides much lower blank signals and high specific signals (i.e. higher signal-to-noise ratio) than prompt fluorescence measurements. Prompt fluorescence (Spectramax Gemini plate reader) showed at least 10-fold lower sensitivity with respect to the probe than time-resolved plate reader. However, the oxygen probe response to the dissolved oxygen and its concentration changes was similar to that of the time-resolved fluorescence detectors. Therefore, the probes can be used on such instruments, and also within a broad range of concentrations.

EXAMPLE 6

Synthesis of Oxygen Probes Based on Monofunctional Maleimide Derivative of Pt-coproporphyrin and Mono-thiol-PEG PtCP-maleimide was dissolved in DMSO at a concentration of 5 mg/ml ($5 \times 10^{-3}$M). 100 ul of this solution was added to 900 ul of $CH_3O$-PEG-NH—CO—$C_2H_4$—SH (M.W. 5,000 or 20,000) in 0.15 M phosphate buffer, pH 7.8(1:7 mg/ml, $2.55 \times 10^{-5}$M) and the resulting reaction mixture was incubated at room temperature for 2 hours in dark place and then separated on a Sephadex G-25 desalting column equilibrated with phosphate buffer, pH 7.4. Fractions of the PEG-PtCP conjugate were collected, desalted and freeze dried for long-term storage.

EXAMPLE 7

Synthesis of Oxygen Probes Based on Monofunctional Carboxylic Derivative of Pt-coproporphyrin and Mono-amino PEG PtCP-mono-acid-trimethylester was dissolved in DMSO at a concentration of 5 mg/ml ($5 \times 10^{-3}$M). Dicyclohexylcarbodiimide was added to this solution at a concentration 5 mg/ml (~$1.5 \times 10^{-2}$M) to activate the carboxylic group of PtCP. 100 ul of this solution was added to 900 ul of $CH_3O$-PEG-$NH_2$ (M.W. 5,000 or 20,000) chloroform (1.7 mg/ml, $2.55 \times 10^{-5}$M) and the resulting reaction mixture was incubated at room temperature for 2 hours in dark place. After that, the PEG-PTCP conjugate formed was purified by precipitation with 10-fold excess of diethyl ether, which was repeated 3 times. Purified PEG-PtCP conjugate was then dried, re-dissolved in water, filtered, dried on vacuum centrifuge, and stored at +4° C. in the dark.

EXAMPLE 8

Synthesis of Oxygen Probes Based on Monofunctional Isothiocyanatophenyl Derivative of Palladium(II)-coproporphyrin and Amino-PEG PdCP-NCS was dissolved in DMSO at a concentration of 5 mg/ml (~$5 \times 10^{-3}$M). 100 ul of this solution was added to 900 ul of $CH_3O$-PEG-$NH_2$ (M.W. 5,000 or 20,000) in 0.05 M carbonate buffer, pH 9.6(1.7 mg/ml, $2.55 \times 10^{-5}$M) and the resulting reaction mixture was incubated at room temperature for 2 hours in dark place and then separated on a Sephadex, desalting column equilibrated with phosphate buffer, pH 7.4. Fractions of the PEG-PdCP conjugate were collected, desalted and freeze dried for long-term storage.

When changing from air-saturated to deoxygenated solution, this probe was shown to produce ~5-time greater phosphorescence quenching by ambient oxygen than PtCP-PEG-20,000.

EXAMPLE 9

Application of the Oxygen Probes to Monitoring Cellular Respiration and Cell Viability Assays FL5.12 cells were cultured at a density of $3 \times 10^5$ cells/ml in medium supplemented with 10% fetal bovine serum and interleukin-3 for three days. Cells were then centrifuged, re-suspended in fresh medium and counted using a hemocytometer. Cells were diluted to the desired concentrations in the range of $10^5$-$10^7$ cells/ml with growth medium and dispensed in 150 ul aliquotes into the wells of 96-well plates (Nunc). PtCP-BSA 2:1 or PtCP-PEG-20,000 (1:1) conjugate was then added to each well at a concentration $10^{-6}$ to $10^{-9}$ M (depending on the experiment). The plate was preheated at 37° C. for 10 minutes to allow temperature and gas equilibrium. 100 ul of heavy mineral oil was then placed on top of each sample to reduce the effect of atmospheric oxygen and phosphorescence intensity readings were taken at regular time intervals (1-3 minutes) for a period of 30-120 min. Time profiles thus obtained were used to determine the initial slopes of the phosphorescent signal in each sample, which were then correlated with the rates of oxygen uptake, metabolic activity and viability of cells.

Figure 3:
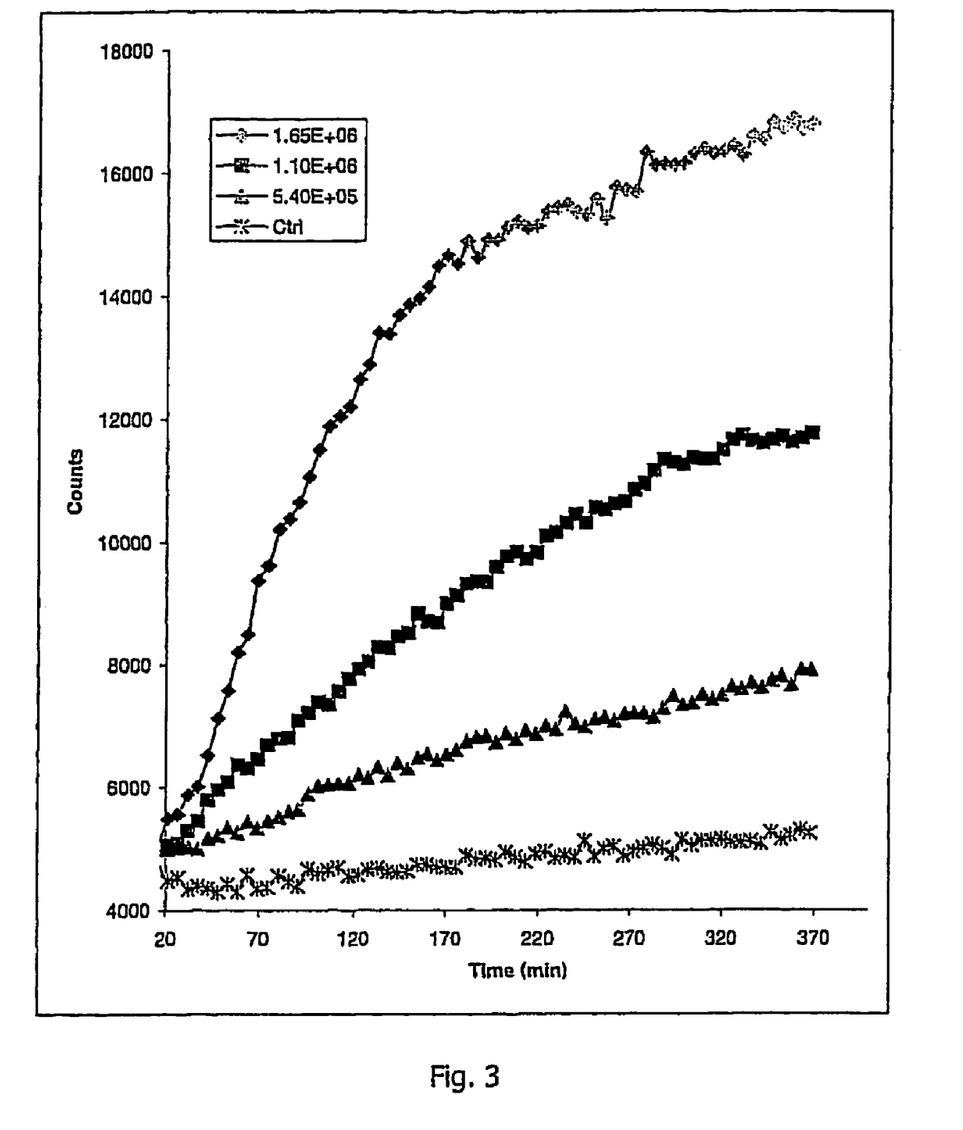
FIG. 3 is a graph showing the respirometric profiles of FL5.12 cells as a function of cell numbers, measured at 37° C. on a time-resolved fluorescence plate reader using the PtCP-PEG oxygen probe.

Measurements of the phosphorescence intensity on a time-resolved fluorescence plate reader were carried out using excitation with 532 nm pulsed laser, 650 nm emission filter, and photon counting detector. Excitation pulse width was set at 10 us, repetition rate—1 kHz, delay time after excitation—20 us, gate time—80 us, integration time—1 s (i.e. 1000 cycles). Results shown in FIG. 3 demonstrate that the oxygen probes provide phosphorescent response to oxygen gradients created by cellular respiration, which correlate with cell numbers.

The high sensitivity of time-resolved fluorescence measurements with respect to PtCP-BSA oxygen probe also allowed pre-coating of plates with this probe by physical adsorption, as it is used in ELISA assays. Thus, plates coated with PtCP-BSA at a concentration of 0.05 ug/ml provided a high phosphorescent signal from the wells (about 9000 counts for air-saturated samples) and were used successfully in cell-respirometric assays, showing a similar response to that observed when the probe was added directly to the test sample (results not shown).

EXAMPLE 10

Assessment of Effector/Drug Action on Cells

Figure 4:
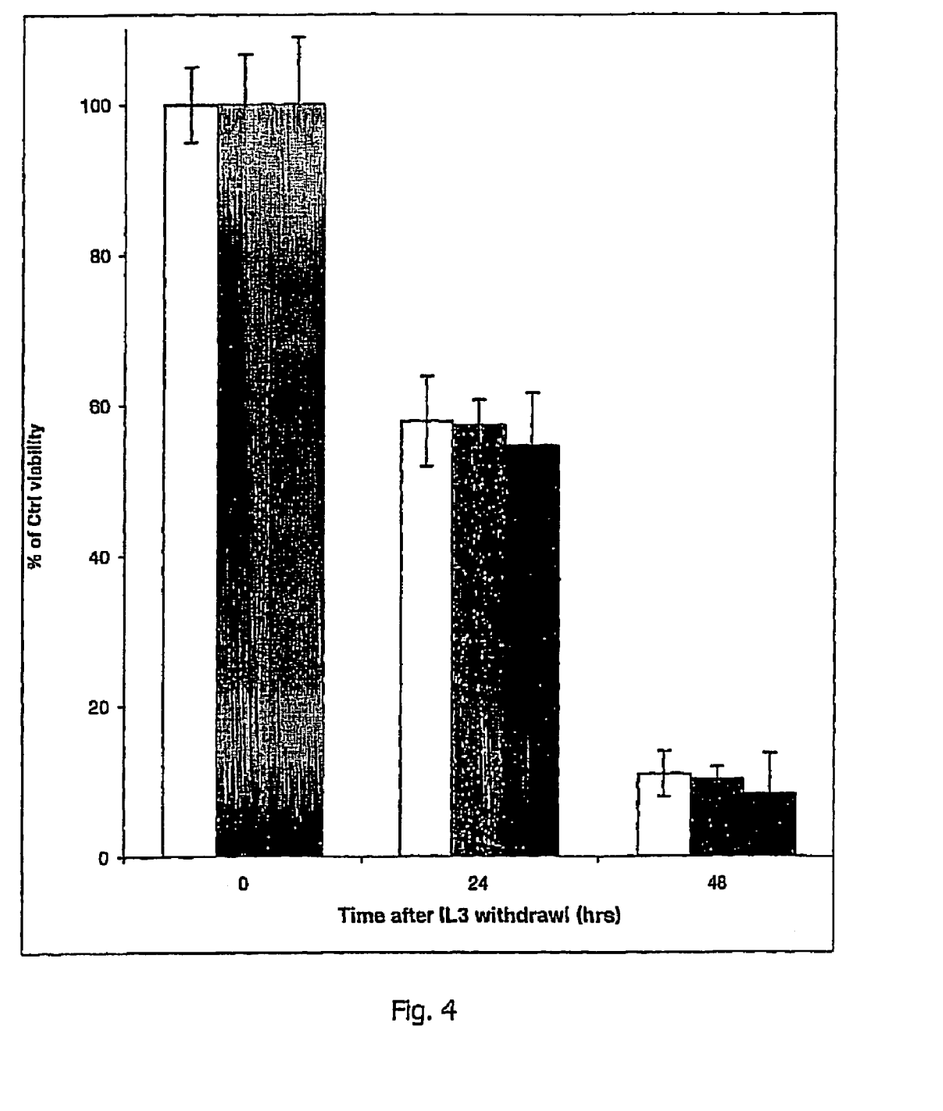
FIG. 4 is a bar chart demonstrating the validity of oxygen consumption analysis (dark bars) in comparison with trypan blue (open bars) and Calcein AM assays (light bars) for the mammalian cells ($1.2 \times 10^6$ cells/ml) treated with effector (interleukin-3). Viability of untreated cells was taken as 100%.

Apoptosis induction by IL-3 withdrawal and cell viability analysis: FL5.12 cells were cultured in 24 well plates at $3 \times 10^5$ cells/ml in Iscove's modified defined medium containing 5% FBS with and without 10% IL-3. At the indicated times, viability was determined in parallel by the three different methods: 1) oxygen cell respirometry as described in example 9, 2) Calcein AM membrane integrity assay and 3) counting live and dead cells after trypan blue dye staining. The percentage of viable cells was determined from the total number of cells per well, and all data represent the mean for triplicate cultures for each of the time points. Results shown in FIG. 4 indicate that the oxygen probes and method provide adequate information about the response of test cells to drug/effector action, which correlate well with other cell viability assays.

EXAMPLE 11

Assessment of Cytotoxicity of the Oxygen Probes

Figure 5:
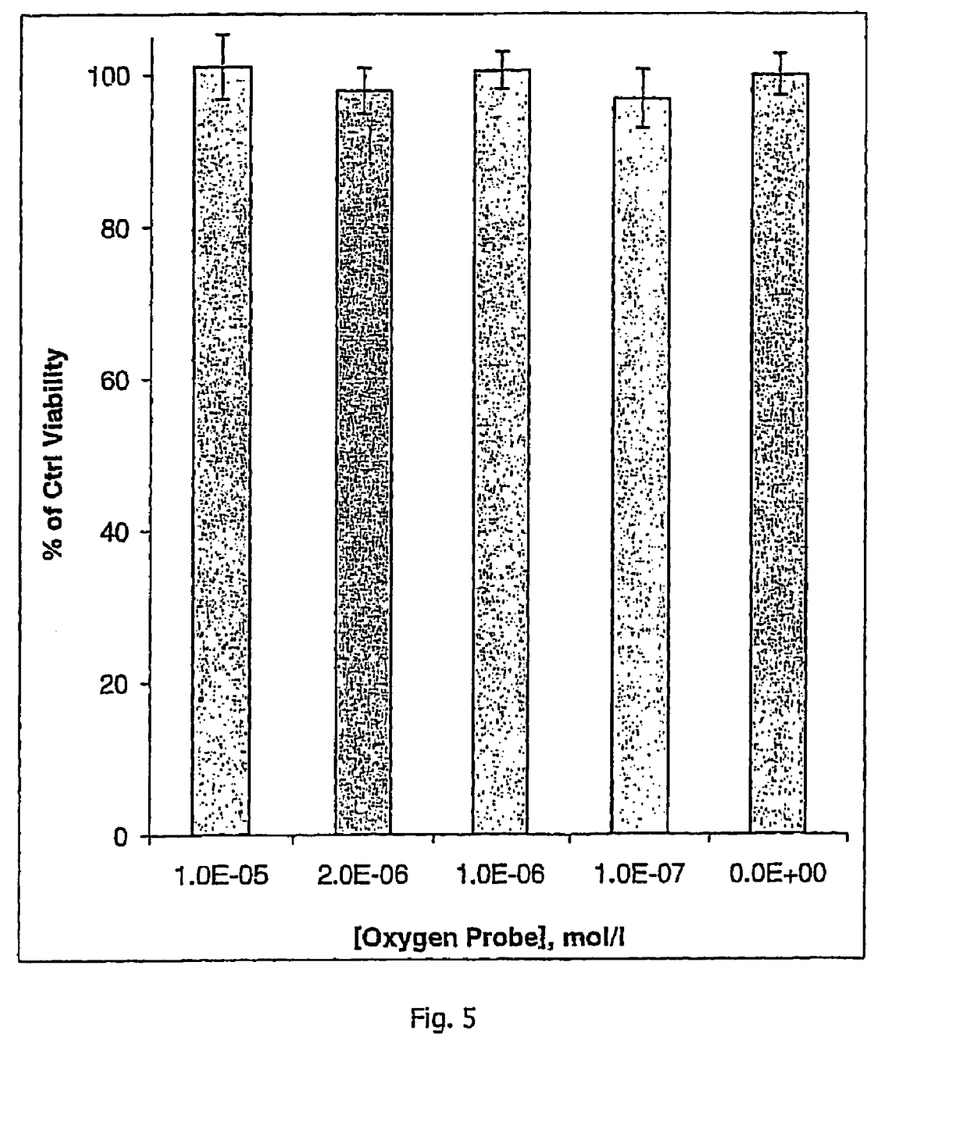
FIG. 5 is a bar chart showing the effect of PtCP-BSA probe concentrations on the viability of FL5.12 cells in conditions of a typical cell-respirometric assay.

Samples of FL5.12 cells in Iscove's modified defined medium ($7 \times 10^5$ cells/ml) were incubated with different concentrations of PtCP-BSA, PtCP-PEG and PtCP-dextran oxygen probes ($10^{-5}$M to $10^{-7}$M) in the microplate for 2.5 hours at 37° C., during which the samples were scanned every 2 minutes by the plate reader. The viability of FL5.12 cells was then analysed by trypan blue staining. In these conditions mimicking a typical cell-respirometric experiment all the oxygen probes showed no detectable cyto- and phototoxic action on the sensitive mammalian cells. Results of a typical experiment are shown in FIG. 5.

EXAMPLE 12

Monitoring Enzymatic Reaction with the Oxygen Probes

Figure 6:
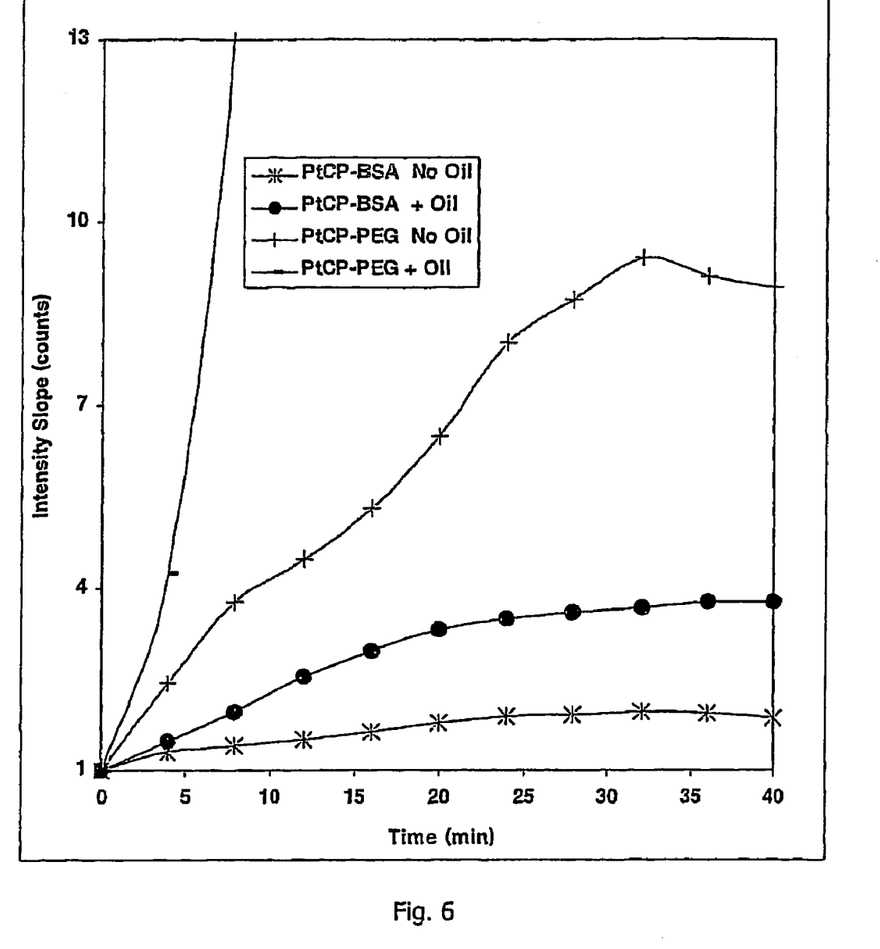
FIG. 6 is a graph showing the performance of the PtCP-BSA and PtCP-PEG probes in monitoring of reaction of glucose oxidation catalised by glucose oxidase enzyme.

Phosphate buffer saline, pH 7.4 containing 10 mM of D-glucose was dispensed in 150 ul aliquotes into the wells of 96-well plates (Nunc). PtCP-BSA or PtCP-PEG probe were then added to the wells at a concentration $10^{-6}$M. The plate was preheated at 37° C. for 10 minutes to allow temperature and gas equilibrium and then glucose oxidase enzyme was added to each well at concentration 0.1 ug/ml. 100 ul of heavy mineral oil was then placed on top of some samples (to reduce the effect of atmospheric oxygen), while the others were left without oil. Phosphorescence intensity readings were taken at regular time intervals (1-3 minutes) for a period of 30-120 min. Results shown in FIG. 6 indicate that the mineral oil seal improves assay sensitivity and that PtCP-PEG probe provides greater signal changes than the PtCP-BSA probe.

EXAMPLE 13

Synthesis of Oxygen Probes Based on Monofunctional Pt-coproporphyrin and Monoclonal Antibodies to CD4 Receptors on T Cells Labelling of monoclonal antibodies with PtCP-NCS and purification of the resulting conjugate were carried out as described in the example 1, but using 4 times more dye than with BSA (200 ul rather than 50 ul). Similarly to the PtCP-BSA probe described in example 1, the PtCP-antibody conjugate (1.4:1) produced phosphorescent response to changes in the dissolved oxygen concentration in the sample. The conjugate also had the ability to bind to T cells bearing CD4 receptors, but not bind to other cells lacking this receptor. CD4+ cells stained with the conjugate can be visualized on a fluorescent microscope. When bound to the cells, the conjugate essentially retained its sensitivity to oxygen concentration in the aqueous sample.

EXAMPLE 14

Monitoring of Oxygen Respiration of Aquatic Organisms Using the Oxygen Probes

The brine shrimps Artemia salina (size~1 mm) were placed in the wells of standard 384-well microtitre plates—five animals in 50 ul of artificial seawater in each well, together with 1 uM of the PtCP-PEG oxygen probe. Artemia were exposed to different concentrations of the toxicants (heavy metals, drugs) for approximately 20 min at ambient temperature, then a 50 ul layer of heavy mineral oil was applied to seal the samples from ambient air oxygen. The samples were then monitored on a fluorescence plate reader (Spectramax Gemini, Molecular Devices) at 30° C. for 1-2 h. (excitation/emission wavelengths—380/650 nm), to establish oxygen gradients. Measured oxygen gradients of treated Artemia were compared to those of the untreated samples (controls), to determine changes in viability of Artemia as a result of the treatment.

The invention is not limited to the embodiments hereinbefore described which may be varied in detail.

What is claimed is:

1. An oxygen sensitive probe comprising a monofunctional derivative of an oxygen sensitive photoluminescent dye covalently attached to a water soluble hydrophilic macromolecular carrier selected from the group comprising a polypeptide, a polysaccharide, and a poly(ethyleneglycol), the oxygen-sensitive photoluminescent dye including a single reactive chemical group for chemical conjugation to the macromolecular carrier and the oxygen sensitive photoluminescent dye being a monofunctional p-isothiocyantophenyl derivative of Pt-coproporphyrin-I.

2. The probe as claimed in claim 1, wherein the dye has an emission lifetime in the order of 10 to 100 microseconds in deoxygenated aqueous solution.

3. The probe as claimed in claim 1, wherein the macromolecular carrier and oxygen sensitive dye are present in a ratio of close to 1:1 to 1:2.

4. The oxygen sensitive probe as claimed in claim 1, in combination with another probe.

5. A method for monitoring oxygen uptake by chemical or biological samples comprising the step of adding an oxygen sensitive probe to a test sample and measuring changes in the probe emission which reflect changes in the dissolved oxygen concentration, wherein the probe comprises a monofunctional derivative of an oxygen-sensitive photoluminescent dye covalently attached to a water-soluble hydrophilic macromolecular carrier wherein the probe is a probe as claimed in claim 2.

6. The probe as claimed in claim 1, wherein the macromolecular carrier comprises a reactive chemical group for chemical conjugation to the monofunctional derivative of an oxygen sensitive photoluminescent dye.

7. The probe as claimed in claim 6, wherein the reactive chemical group is selected from: an amino group, a thiol group, and an N-succinimide group.

8. The probe as claimed in claim 1, wherein the macromolecular carrier is a monofunctional macromolecular carrier.

9. The probe as claimed in claim 1, wherein the macromolecular carrier comprises poly(ethyleneglycol) (PEG) having a molecular mass exceeding 2,000 Da.

10. The probe as claimed in claim 9, wherein the macromolecular carrier comprises any one or more of PEG-5,000 or PEG-20,000.

11. The probe as claimed in claim 9, wherein the macromolecular carrier comprises PEG with one terminal amino group.

12. The probe as claimed in claim 9, wherein the macromolecular carrier comprises PEG with one terminal thiol group.

13. The probe as claimed in claim 9, wherein the macromolecular carrier comprises activated PEG containing one or two terminal N-succinimide group.

14. The probe as claimed in claim 1, wherein the macromolecular carrier comprises a polypeptide having molecular weight above 5,000 dalton.

15. The probe as claimed in claim 14, wherein the macromolecular carrier comprises albumin or immunoglobulin.

16. The probe as claimed in claim 1, wherein the macromolecular carrier comprises dextran or amino-dextran having molecular mass exceeding 5,000 Da.

17. The probe as claimed in claim 1, wherein the macromolecular carrier is capable of recognising and specifically binding to the surface of a particular cell or group of cells in a sample.

18. An oxygen sensitive probe comprising a monofunctional derivative of an oxygen sensitive photoluminescent dye covalently attached to a water soluble hydrophilic macromolecular carrier selected from the group comprising a polypeptide, a polysaccharide, and a poly(ethyleneglycol), the oxygen sensitive photoluminescent dye including a single reactive chemical group for chemical conjugation to the macromolecular carrier and the oxygen sensitive photoluminescent dye being a monofunctional amino, maleimido-, or N-succinimido-derivative of Pt-coproporphyrin-I.

19. The probe as claimed in claim 18, wherein the dye has an emission lifetime in the order of 10 to 100 microseconds in deoxygenated aqueous solution.

20. The probe as claimed in claim 18, wherein the macromolecular carrier and oxygen sensitive dye are present in a ratio of close to 1:1 to 1:2.

21. The oxygen sensitive probe as claimed in claim 18, in combination with another probe.

22. The probe as claimed in claim 18, wherein the macromolecular carrier comprises a reactive chemical group for chemical conjugation to the monofunctional derivative of an oxygen sensitive photoluminescent dye.

23. The probe as claimed in claim 22, wherein the reactive chemical group is selected from: an amino group, a thiol group, and an N-succinimide group.

24. The probe as claimed in claim 18, wherein the macromolecular carrier is a monofunctional macromolecular carrier.

25. The probe as claimed in claim 18, wherein the macromolecular carrier comprises a polypeptide having molecular weight above 5,000 dalton.

26. The probe as claimed in claim 25, wherein the macromolecular carrier comprises albumin or immunoglobulin.

27. The probe as claimed in claim 18, wherein the macromolecular carrier comprises dextran or amino-dextran having molecular mass exceeding 5,000 Da.

28. The probe as claimed in claim 18, wherein the macromolecular carrier is capable of recognising and specifically binding to the surface of a particular cell or group of cells in a sample.

29. An oxygen sensitive probe comprising a monofunctional derivative of an oxygen sensitive photoluminescent dye covalently attached to a water soluble hydrophilic macromolecular carrier, the macromolecular carrier including poly (ethyleneglycol) (PEG) having a molecular mass exceeding 2,000 Da.

30. The probe as claimed in claim 29, wherein the macromolecular carrier comprises any one or more of PEG-5,000 or PEG-20,000.

31. The probe as claimed in claim 29, wherein the macromolecular carrier comprises PEG-20,000 with one terminal amino group.

32. The probe as claimed in claim 29, wherein the macromolecular carrier comprises activated PEG-20,000 containing one or two terminal N-succinimide group.

33. The probe as claimed in claim 29, wherein the oxygen sensitive probe is conjugated to the terminal group(s) of a high molecular weight PEG to give predominantly a 1:1 or 2:1 conjugate.

34. The probe as claimed in claim 29, wherein the dye has an emission lifetime in the order of 10 to 100 microseconds in deoxygenated aqueous solution.

35. The probe as claimed in claim 29, wherein the macromolecular carrier and oxygen sensitive dye are present in a ratio of close to 1:1 to 1:2.

36. The oxygen sensitive probe as claimed in claim 29, in combination with another probe.

37. The probe as claimed in claim 29, wherein the macromolecular carrier comprises poly(ethyleneglycol) (PEG) having a molecular mass exceeding 2,000 Da.

38. The probe as claimed in claim 37, wherein the macromolecular carrier comprises any one or more of PEG-5,000 or PEG-20,000.

39. The probe as claimed in claim 37, wherein the macromolecular carrier comprises PEG with one terminal amino group.

40. The probe as claimed in claim 37, wherein the macromolecular carrier comprises PEG with one terminal thiol group.

41. The probe as claimed in claim 37, wherein the macromolecular carrier comprises activated PEG containing one or two terminal N-succinimide group.

42. The probe as claimed in claim 29, wherein the oxygen sensitive photoluminescent dye is a monofunctional derivative of Pt-coproporphyrin-I.

43. The probe as claimed in claim 29, wherein the oxygen sensitive photoluminescent dye comprises a single reactive chemical group for chemical conjugation to the macromolecular carrier.

44. The probe as claimed in claim 29, wherein the oxygen sensitive photoluminescent dye is selected from: a monofunctional p-isothiocyanatophenyl derivative of Pt-coproporphyrin-I, a monofunctional amino derivative of Pt-coproporphyrin-I, a monofunctional maleimido derivative of Pt-coproporphyrin-I, a monofunctional N-succinimido derivative of Pt-coproporphyrin-I, and a monofunctional carboxylic derivative of Pt-coproporphyrin-I.

45. The probe as claimed in claim 29, wherein the macromolecular carrier comprises a reactive chemical group for chemical conjugation to the monofunctional derivative of an oxygen sensitive photoluminescent dye.

46. The probe as claimed in claim 45, wherein the reactive chemical group is selected from: an amino group, a thiol group, and an N-succinimide group.

47. The probe as claimed in claim 29, wherein the macromolecular carrier is a monofunctional macromolecular carrier.

48. The probe as claimed in claim 29, wherein the macromolecular carrier comprises PEG with one terminal thiol group.

49. The probe as claimed in claim 29, wherein the macromolecular carrier comprises PEG with one terminal amino group.

50. The probe as claimed in claim 29, wherein the macromolecular carrier comprises activated PEG containing one or two terminal N-succinimide group.

51. The method as claimed in claim 5, wherein the biological sample contains cells, microorganisms, subcellular organells, animal tissue or aquatic animals.

52. The method as claimed in claim 5, wherein prior to or after addition of the oxygen probe the sample is treated with a drug, hormone, or other effector(s).

53. The method as claimed in claim 5, for determining the number of cells, cell viability, drug or effector action on cells in a sample.

54. The method as claimed in claim 5, wherein the biological sample contains an oxygen dependent enzyme or enzymatic system and corresponding substrate(s).

55. The method as claimed in claim 54, for determining the concentration of enzyme substrate, or the rate of metabolism of this substrate.

56. The method as claimed in claim 54, for determining enzyme activity or inhibition.

57. The method as claimed in claim 5, wherein the luminescent intensity of the oxygen probe is monitored.

58. The method as claimed in claim 5, wherein the luminescent signal of the oxygen probe is measured by time-resolved fluorescence with microsecond time resolution.

59. The method as claimed in claim 58, wherein the delay and gate times are comparable with the lifetime of the oxygen probe in an air-saturated sample.

60. The method as claimed in claim 58, wherein time-resolved measurements of the oxygen probe are carried out at least two different gate times after excitation.

61. The method as claimed in claim 58, wherein the probe response to oxygen is optimised by optimising the parameters of time-resolved fluorescence measurements, namely the delay and/or gate time.

62. The method as claimed in claim 57, wherein the luminescent signal of the oxygen probe is measured using phase modulation technique.

63. The method as claimed in claim 57, wherein excitation of the oxygen probe is performed by a laser compatible with the probe.

\* \* \* \* \*